(12) United States Patent
Frey et al.

(10) Patent No.: US 10,118,883 B2
(45) Date of Patent: Nov. 6, 2018

(54) METHOD FOR PRODUCING LEVULINIC ACID FROM LIGNOCELLULOSIC BIOMASS

(71) Applicant: Georgia-Pacific LLC, Atlanta, GA (US)

(72) Inventors: William A. Frey, Atlanta, GA (US); Jeffrey Wayne Brown, Peachtree City, GA (US); John Patrick Kelly, Sugar Hill, GA (US); Michael Eugene Carroll, Loganville, GA (US); Peter Chester Guion, Alpharetta, GA (US)

(73) Assignee: Georgia-Pacific LLC, Atlanta, GA (US)

( * ) Notice: Subject to any disclaimer, the term of this patent is extended or adjusted under 35 U.S.C. 154(b) by 338 days.

(21) Appl. No.: 14/384,548

(22) PCT Filed: Mar. 11, 2013

(86) PCT No.: PCT/US2013/030141
§ 371 (c)(1),
(2) Date: Sep. 11, 2014

(87) PCT Pub. No.: WO2013/138222
PCT Pub. Date: Sep. 19, 2013

(65) Prior Publication Data
US 2015/0052806 A1  Feb. 26, 2015

Related U.S. Application Data

(60) Provisional application No. 61/609,601, filed on Mar. 12, 2012.

(51) Int. Cl.
*C07C 51/00* (2006.01)
*F23G 7/00* (2006.01)
(Continued)

(52) U.S. Cl.
CPC .............. *C07C 51/00* (2013.01); *C07C 51/42* (2013.01); *C10L 5/403* (2013.01); *D21C 3/022* (2013.01);
(Continued)

(58) Field of Classification Search
USPC .............................. 110/346; 44/606; 562/515
See application file for complete search history.

(56) References Cited

U.S. PATENT DOCUMENTS 3,122,933 A   3/1964  Rodgers
3,258,481 A   6/1966  Sassenrath et al.
(Continued)

FOREIGN PATENT DOCUMENTS

RU    2200149 C2    3/2003
SU     211724 A    11/1968
(Continued)

OTHER PUBLICATIONS

PCT/US2013/030141 International Search Report and Written Opinion, dated Jun. 13, 2013 (10 pages).
(Continued)

*Primary Examiner* — Ellen McAvoy
*Assistant Examiner* — Chantel Graham
(74) *Attorney, Agent, or Firm* — Ram W. Sabnis

(57) ABSTRACT

A method for producing levulinic acid from lignocellulosic biomass comprising hemicellulose including one or more six carbon chain compound precursors comprises the steps of hydrolyzing the lignocellulosic biomass to form a first phase comprising partially hydrolyzed lignocellulosic biomass including cellulose and lignin and a second phase comprising one or more five carbon chain sugars and one or more six carbon chain sugars from degradation of the hemicellulose, (Continued)

separating the first phase from the second phase, and converting at least a portion of the one or more six carbon chain sugars to levulinic acid.

16 Claims, 1 Drawing Sheet

(51) Int. Cl.
*D21C 3/02* (2006.01)
*C07C 51/42* (2006.01)
*C10L 5/40* (2006.01)

(52) U.S. Cl.
CPC ............ *F23G 7/00* (2013.01); *C10L 2290/08* (2013.01); *Y02E 50/30* (2013.01)

(56) References Cited

U.S. PATENT DOCUMENTS

| | | | |
|---|---|---|---|
| 3,314,797 | A | 4/1967 | Hess et al. |
| 3,701,789 | A | 10/1972 | Ramos-Rodriguez |
| 4,470,851 | A | 9/1984 | Paszner et al. |
| 4,897,497 | A | 1/1990 | Fitzpatrick |
| 5,503,709 | A | 4/1996 | Burton |
| 5,562,777 | A | 10/1996 | Farone et al. |
| 5,608,105 | A | 3/1997 | Fitzpatrick |
| 5,705,369 | A | 1/1998 | Torget et al. |
| 6,423,145 | B1 | 7/2002 | Nguyen et al. |
| 6,660,506 | B2 | 12/2003 | Nguyen et al. |
| 7,378,549 | B2 | 5/2008 | Ayoub |
| 7,402,224 | B1 | 7/2008 | Avignon et al. |
| 7,666,637 | B2 | 2/2010 | Nguyen |
| 7,824,521 | B2 | 11/2010 | van Heiningen et al. |
| 8,030,039 | B1 | 10/2011 | Retsina et al. |
| 8,053,566 | B2 | 11/2011 | Belanger et al. |
| 8,158,833 | B2 | 4/2012 | Dumenil et al. |
| 2010/0234638 | A1 | 9/2010 | Fitzpatrick |
| 2010/0279361 | A1 | 11/2010 | South et al. |
| 2010/0312006 | A1 | 12/2010 | Lake et al. |
| 2010/0330633 | A1 | 12/2010 | Walther et al. |
| 2011/0144359 | A1 | 6/2011 | Heide et al. |
| 2011/0172475 | A1 | 7/2011 | Peters et al. |
| 2011/0183389 | A1 | 7/2011 | van Walsum et al. |
| 2011/0195468 | A1 | 8/2011 | Retsina et al. |
| 2011/0250637 | A1 | 10/2011 | Kurihara et al. |
| 2011/0287493 | A1 | 11/2011 | Marzialetti et al. |
| 2011/0318796 | A1 | 12/2011 | Walther |
| 2012/0009632 | A1 | 1/2012 | Retsina et al. |
| 2012/0302767 | A1 | 11/2012 | Dumesic et al. |

FOREIGN PATENT DOCUMENTS

| | | |
|---|---|---|
| WO | 9819986 A1 | 5/1998 |
| WO | 2007065241 A1 | 6/2007 |
| WO | 2009/156842 A1 | 12/2009 |

OTHER PUBLICATIONS

Walton, Sara Lynn, "Biological Conversion of Hemicellulose Extract into Value-Added Fuels and Chemicals" (Dec. 1, 2009), Electronic Theses and Dissertations, Paper 226 (175 pages).

Humbird, D., et al., "Process Design and Economics for Biochemical Conversion of Lignocellulosic Biomass to Ethanol—Dilute-Acid Pretreatment and Enzymatic Hyrdolysis of Corn Stover," National Renewable Energy Laboratory, Technical Report NREL/TP-5100-4464, May 2011 (147 pages).

Girisuta, B., "Levulinic acid from lignocellulosic biomass," University of Gronigen, Scientific, Doctoral Thesis (Nov. 5, 2007) (25 pages).

International Search Report and Written Opinion of PCT/US2013/030141, dated Dec. 9, 2013.

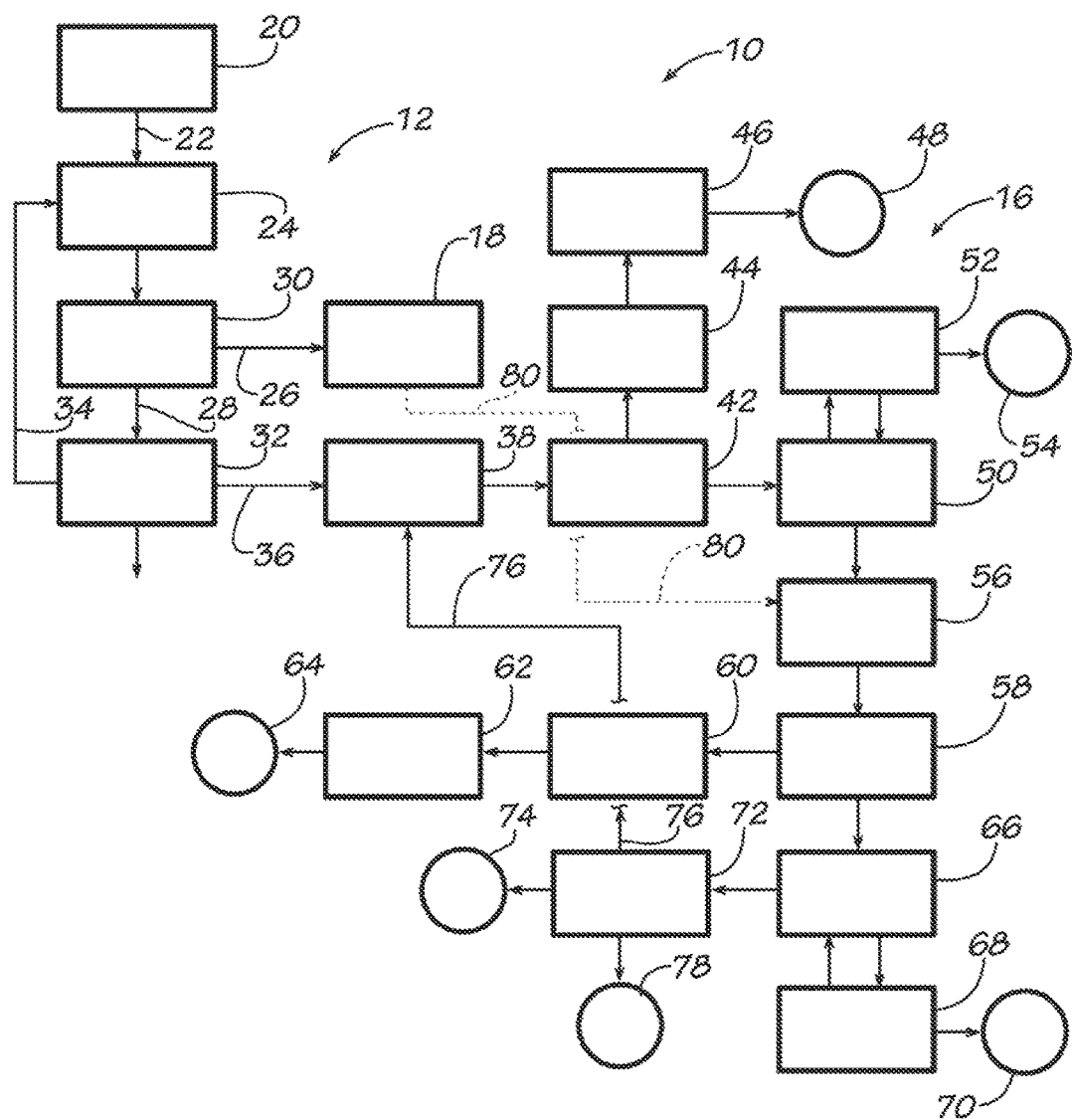

METHOD FOR PRODUCING LEVULINIC ACID FROM LIGNOCELLULOSIC BIOMASS

CROSS-REFERENCE TO RELATED APPLICATIONS

This is a submission pursuant to 35 U.S.C. 154(d)(4) to enter the national stage under 35 U.S.C. 371 for PCT/US2013/030141, filed Mar. 11, 2013. Priority is claimed under 35 U.S.C. 119(a) and 35 U.S.C. 365(b) to U.S. Provisional Patent Application No. 61/609,601, filed Mar. 12, 2012. The subject matters of International Application No. PCT/US2013/030141 and U.S. Provisional Patent Application No. 61/609,601 are expressly incorporated herein by reference.

TECHNICAL FIELD

This invention relates to the production of levulinic acid from lignocellulosic biomass comprising hemicellulose including one or more six carbon chain compound precursors.

BACKGROUND OF THE INVENTION

In pulp and papermaking, lignocellulosic biomass, such as soft wood trees, is separated into cellulose, which is used to make the pulp and paper products, and a mixture of lignin and hemicellulose, which are typically combusted as fuel. The lignin and hemicellulose portion of the lignocellulosic biomass in the pulp and papermaking process is removed from the pulp and papermaking process as a by-product called black liquor. The value of black liquor as a combustible fuel is limited and a method of converting black liquor to one or more higher value products in a cost effective manner is desirable. Accordingly, a need exist for cost effectively converting at least a portion of black liquor to one or more products having a higher value than use of black liquor as a combustible fuel.

SUMMARY

This invention encompasses a method for producing levulinic acid from lignocellulosic biomass comprising hemicellulose including one or more six carbon chain compound precursors, the method comprising the steps of hydrolyzing the lignocellulosic biomass to form one or more six carbon chain sugars from degradation of hemicellulose and converting at least the portion of one or more six carbon chain sugars to levulinic acid. According to an embodiment of this disclosure, the step of hydrolyzing the lignocellulosic biomass forms a first phase comprising partially hydrolyzed lignocelluosic biomass including cellulose and lignin and a second phase comprising one or more five carbon chain sugars and the one or more six carbon chain sugars from degradation of hemicellulose and the method for producing levulinic acid further comprises separating the first phase from the second phase. According to an embodiment of this disclosure, the method for producing levulinic acid further includes converting at least a portion of the one or more five carbon chain sugars to furfural, a furfural reaction intermediate, tar, or a combination thereof in the presence the one or more six carbon chain sugars, separating at least a portion of the furfural, the furfural reaction intermediate, the tar, or the combination thereof from the one or more six carbon chain sugars, before converting at least a portion of the one or more six carbon chain sugars to levulinic acid. According to still another embodiment of this disclosure, an integrated method for producing wood pulp product and levulinic acid from lignocellulosic biomass comprises the steps of making the levulinic acid as described above and converting at least a portion of the first phase comprising partially hydrolyzed lignocelluosic biomass including cellulose and lignin to a wood pulp product. According to yet another embodiment of this disclosure, the integrated method for producing wood pulp product and levulinic acid from lignocellulosic biomass further comprises the steps of separating the five carbon chain sugars from the six carbon chain sugars and combining the five carbon chain sugars with the wood pulp product.

These and other features, aspects, and advantages of the present invention and embodiments thereof will become better understood when the following detailed description is read with reference to the accompanying drawing, where the components are not necessarily to scale and in which corresponding reference numerals designate corresponding parts throughout the drawings.

BRIEF DESCRIPTION OF DRAWING

FIG. 1 is schematic diagram of an integrated system for producing wood pulp product and levulinic acid from lignocellulosic biomass according to an embodiment of this invention.

DETAILED DESCRIPTION OF EMBODIMENTS

In the following description, numerous specific details are given to provide a thorough understanding of embodiments. The embodiments can be practiced without one or more specific details, or with other methods, components, materials, and the like. In other instances, well known structures, materials, or operations are not shown or described in detail to avoid obscuring aspects of the embodiments.

Reference throughout the specification to "one embodiment," "an embodiment," or "embodiments" means that a particular feature, structure, or characteristic described in connection with the embodiment is included in at least one embodiment. Thus, the appearances of the phases "in one embodiment" or "in an embodiment" in various places throughout the specification are not necessarily referring to the same embodiment. Furthermore, the particular features, structures, or characteristics may be combined in any suitable manner in one or more embodiments.

FIG. 1 is a schematic diagram of an integrated system 10 for producing wood pulp product and levulinic acid from lignocellulosic biomass generally comprising a lignocellulosic biomass hydrolysis system 12, a five and six carbon chain sugar conversion system 16, and a wood pulp product production system 18. Integration of a system for converting lignocellulosic biomass to levulinic acid into an existing wood pulp product production system in accordance with embodiments of this disclosure may allow the production of levulinic acid with less capital investment and operating expense and may allow operating cost savings in addition to producing a valuable product in levulinic acid. This will be explained in more detail below.

The biomass hydrolysis system 12 comprises a biomass feed system 20 for delivering lignocellulosic biomass 22 to a biomass hydrolysis reaction system 24.

Suitable lignocellulosic biomass materials for producing levulinic acid comprise hemicellulose including one or more six carbon chain compound precursors. The six carbon chain compound precursor or precursors in the hemicellulose can be converted to six carbon chain sugars. Examples of suitable lignocellulosic biomass materials include any biological materials comprising lignocellulose that includes six carbon chain compound precursor-containing hemicellulose such as softwood from trees, softwood chips, slash or hog fuel from softwood tree processing, forest residue, straw, chaff, grain, grasses, corn, corn husk, weeds, aquatic plants, and hay, and lignocellulose containing material of biological origin, such as some municipal waste or household waste.

Some lignocellulosic biomass materials have a higher six carbon chain sugar content for a greater yield of levulinic acid; therefore, selection of higher six carbon chain sugar content lignocellulosic biomass can result in higher levulinic acid yields and efficiency. For example, southern softwood includes a greater concentration of six carbon chain compounds in the hemicellulose portion than does hardwood. Therefore, southern softwood enables a higher yield of levulinic acid than does hardwood biomass.

If necessary, the particle size of the lignocellulosic biomass material can be reduced before introduction into the biomass hydrolysis reaction system 24. Any manner known to be suitable to the skilled person can be used to reduce the particle size of the lignocellulosic biomass material. Examples of such methods include crushing, grinding, milling, cutting, chipping, shredding, granulation, and any combination thereof.

Although not shown separately, the biomass feed system 20 can include a turpentine extractor to remove turpentine from softwood biomass. The structure and operation of turpentine extractors are well known to those skilled in the art.

According to an embodiment of this disclosure, the biomass hydrolysis reaction system 24 hydrolyzes the lignocellulosic biomass to form a first phase 26 comprising partially hydrolyzed lignocelluosic biomass comprising cellulose and lignin and a second phase 28 comprising one or more five carbon chain sugars and one or more six carbon chain sugars from degradation of hemicellulose in the lignocellulosic biomass. According to an embodiment of this disclosure, the step of hydrolyzing the lignocellulosic biomass in the hydrolysis reaction system 24 may comprise contacting the lignocellulosic biomass with steam, a combination of steam and at least one acid, alcohol, or a combination of alcohol and at least one acid. Suitable acids include mineral acids such as hydrochloric acid, nitric acid, phosphoric acid, sulfuric acid, and the like, and organic acids such as acetic acid, formic acid, and the like. According to the embodiments of this disclosure, the acid may be added to the lignocellulosic biomass in an amount from about 0 to about 10% by weight of the lignocellulosic biomass material. According to an embodiment of this disclosure, the acid may be formed from a precursor, such as sulfur dioxide, added to the lignocellulosic biomass material. Suitable alcohols include methanol, ethanol, propanol, butanol, and the like.

The reaction parameters for the hydrolysis in the biomass hydrolysis reaction system 24 can be set to favor the production of the one or more five and six carbon chain sugars from the lignocellulosic biomass as opposed to a higher order reaction conversion such as to tar or char. In accordance with the embodiment of this disclosure, the lignocellulosic biomass hydrolysis in the biomass hydrolysis reaction system 24 may be carried out at a temperature of about 170° C. to about 185° C. for a duration of about 35 minutes to about 60 minutes or about 35 to 45 minutes.

The first phase 26 produced by hydrolysis in the biomass hydrolysis reaction system 24 is substantially solid and the second phase 28 is substantially liquid and includes a solvent such as water or alcohol or both and any acid or alcohol used in the hydrolysis. This mixture of the first phase 26 and the second phase 28 is fed to a first separator 30 which separates the first phase 26 from the second phase 28. The first separator 30 can be of a type known to those skilled in the art to be suitable for this purpose. For example, the separator 30 can be a screw press, a belt press, a drum filter, a disc filter, or a centrifuge, or the like.

The biomass hydrolysis reactor system 24 can be any type of reactor known to be suitable to those skilled in the art including but, according to an embodiment of this disclosure, it includes a pre-steaming device that receives the lignocellulosic biomass from the biomass feed system 20 and steam to heat the lignocellulosic biomass and begin the hydrolysis. The steam heated lignocellulosic biomass is fed to or near the top of a vertical tube reactor. More steam and optionally acid or alcohol, as described hereinabove, is added to the lignocellulosic biomass in the vertical tube reactor and the biomass is hydrolyzed as it passes from the top to the bottom of the reactor.

According to an embodiment of this disclosure, the first phase 26 comprising the partially hydrolyzed lignocelluosic biomass including cellulose and lignin is delivered to the wood pulp product production system 18 which is described more herein below.

According to an embodiment of this disclosure, the second phase 28 from the first separator 30 is fed to a second separator 32 in which the solvent and acid are separated from the second phase 28 by liquid-liquid extraction and returned as recycled solvent and acid 34 to the biomass hydrolysis system 24 for use in the hydrolysis reaction. The five and six carbon chain sugars 36 are fed from the second separator 32 to the five carbon chain sugar conversion reactor 38 for converting at least a portion of the one or more five carbon chain sugars from the second phase 28 to furfural, a furfural reaction intermediate, tar or a combination thereof in the presence of the one or more six carbon chain sugars from the second phase.

The five carbon chain sugar conversion reactor 38 can be any reactor suitable to one skilled in the art for this purpose. According to embodiments of this disclosure, a five carbon chain sugar conversion reactor 38 can be an autoclave, a plug flow reactor, a batch reactor, or a CSTR (a continuously stirred tank reactor). According to an embodiment of this disclosure, the five carbon chain sugar conversion reactor 38 is a relatively low temperature and retention time reactor to convert at least a portion of the one or more five chain sugars to furfural or tar, or both, without converting the six carbon chain sugars. The reaction parameters of the five carbon chain sugar conversion reactor 38 can be set to favor the conversion of the one or more five carbon chain sugars from the second phase 28 primarily to furfural as opposed to the higher order reaction conversion to tar, or vice versa, and to avoid conversion of the one or more six carbon chain sugars from the second phase. According to an embodiment of this disclosure, this step of converting at least a portion of the one or more five carbon chain sugars to furfural or tar or both is carried out in the five carbon chain sugar conversion reactor 38 at a temperature of about 130° C. to about 300° C. or about 130° C. to about 250° C. and at a pressure high enough so that the reactor contents do not reach their boiling point, such as about 10 psi above the vapor pressure of the liquid in the reactor, for about 35 minutes to about 60 minutes.

According to an embodiment of this disclosure, an acid such as a mineral acid or organic acid is added to the five carbon chain sugar conversion reactor 38 to convert the five carbon chain sugars to furfural or tar or both. Suitable mineral acids include hydrochloric acid, nitric acid, sulfuric acid, phosphoric acid, and the like, and suitable organic acids include, acetic acid, formic acid, and the like, and may be added to the five and six carbon chain sugars in the conversion reactor 38 in an amount of from about 0 to about 10% by weight of the reactor contents or more depending on parameters such as the type of biomass, the particular acid, the temperature in the reactor 38 and the like.

According to an embodiment of this disclosure, the next step in the five and six carbon chain sugar conversion system 16 is delivery of the mixture of the furfural, tar, and six carbon chain sugars from the five carbon chain sugar conversion reactor 38 to a furfural flash evaporator 42 to remove the furfural. Any suitable furfural separation system known to those skilled in the art can be used to separate the furfural from the six carbon chain sugars and tar. According to embodiments of this disclosure, other methods of furfural separation include those such as liquid-liquid extraction, gas stripping, steam stripping, distillation and the like. The furfural can then be captured in a furfural condenser 44, purified in a furfural purifier 46, and stored in a furfural storage container 48. The furfural can be used in ways known to those skilled in the art such as a solvent in chemical processes, a wetting agent, refining, production of lysine, and pesticide, and as a combustion fuel for use in producing heat.

According to an embodiment of this disclosure, the one or more six carbon chain sugars and tar are fed from the furfural flash evaporator 42 to a clarifier 50 for separation of the tar from the six carbon chain sugars. The tar is fed to a filter 52 for dewatering and then to a tar storage container 54. Liquid from the filter 52 is returned to the clarifier 50. The tar can be used as combustion fuel to produce energy or used for any of the known uses of tar.

According to an embodiment of this disclosure, after tar removal, the six carbon chain sugars are fed to a six carbon chain sugar conversion reactor 56 for conversion of the one or more six carbon chain sugars to levulinic acid, formic acid and char. According to an embodiment, this step of converting at least a portion of the one or more six carbon chain sugars to levulinic acid comprises contacting the one or more six carbon chain sugars with at least one mineral acid. Suitable mineral acids include hydrochloric acid, nitric acid, sulfuric acid, phosphoric acid, and the like. The reaction parameters for the conversion reaction in the six carbon chain sugar conversion reactor 56 can be set to favor the production of levulinic acid as opposed to a higher order reaction conversion such as to char. In accordance with still another embodiment of this disclosure, the step of converting at least a portion of the one or more six carbon chain sugars in the conversion reaction system 48 is carried out at a temperature of about 190° C. to about 220° C. or about 200° C. to about 210° C. at a pressure high enough so that the reactor contents do not reach their boiling point, such as about 10 psi above the vapor pressure of the liquid in the reactor, for a duration of about 20 minutes to about 60 minutes.

According to an embodiment of this disclosure, the method of converting at least a portion of one or more of six carbon chain sugars to levulinic acid also produces formic acid and char. The levulinic acid, formic acid, and char may be separated by any method known to those skilled in the art. According to an embodiment of this disclosure, this mixture of levulinic acid, formic acid, and char is fed from the six carbon chain sugar conversion reactor 56 to a flash evaporator 58 for separating the formic acid from the levulinic acid and char. According to embodiments of this disclosure, other methods of formic acid separation include those such as liquid-liquid extraction, gas stripping, steam stripping, distillation and the like. The formic acid can then be captured in a formic acid condenser 60, purified in a formic acid purifier 62, and stored in a formic acid storage container 64. The formic acid can be used in ways known to those skilled in the art such as a preservative, an antibacterial, leather tanning, and chemical synthesis.

According to an embodiment of this disclosure, the mixture of levulinic acid and char is fed from the formic acid flash evaporator to a clarifier 66 for separating the char from the levulinic acid. The char is fed to a filter 68 for dewatering and then to a char storage container 70. Liquid from the filter 68 is returned to the clarifier 66. The char can be used as combustion fuel to produce energy or used for any of the known uses of char.

According to an embodiment of this disclosure, a mixture of the levulinic acid and solvent and any acid used in the six carbon chain sugar reactor 56 is fed from the six carbon chain sugar conversion reactor 56 to a liquid-liquid extraction system 72 for separating the levulinic acid from the solvent and acid. According to embodiments of this disclosure, other methods of levulinic acid separation include those such as gas stripping, steam stripping, distillation, and the like. The levulinic acid can then be stored in a levulinic acid storage container 74. The solvent and acid can be recovered and recycled via conduit 76 for use in other operations such as the five carbon chain sugar conversion reactor 38, as shown in FIG. 1, or alternatively, the six carbon chain sugar conversion reactor 56? In some embodiments, the mixture fed to the extraction distillation system 72 may include other residual substances which may also be separated and stored in a residual substance container 78. Such residual substance can also be used as a combustion fuel to produce heat.

Levulinic acid is useful in synthesis of polymers, pharmaceuticals, and chemical commodities such as methyltetrahydrofuran, valerolactone, and ethyl levulinate. Levulinic acid is also a photosensitizer for photodynamic therapy.

According to an embodiment of this disclosure, partially hydrolyzed lignocelluosic biomass from the first phase 26 discharged from the first separator 30 can be diverted from the wood pulp product production system 18 and fed to the six carbon chain sugar conversion reactor 56 via conduit 80 for conversion of six carbon chain sugars or sugar precursors in the partially hydrolyzed lignocelluosic biomass to levulinic acid and formic acid and the remaining partially hydrolyzed lignocelluosic biomass to char and other byproducts.

Integration of the above-described method for producing levulinic acid from lignocellusic biomass in a wood pulp product production system 18 provides several advantages. In a particular embodiment, the step of converting at least a portion of the first phase 26 from the hydrolyzing step to pulp comprises converting the at least a portion of the first phase to pulp in a Kraft pulpmaking process. In such a pulp production process, the recovery boiler, which processes the black liquor and recovers caustic for recycling and reuse in the process, may be the rate limiting step in the pulp making process. According to an embodiment of this disclosure, production of levulinic acid from lignocellulosic biomass in accordance with embodiments of this disclosure prior to delivery of the cellulose and lignin to a wood pulp product production system such as a pulp mill may reduce the amount of black liquor delivered to the recovery boiler by about 10 to 15%. This may directly increase the throughput of the pulp making process. In addition, levulinic acid is a higher value product and may increase the profitability of the overall process. For example, a pulp mill that uses approximately 3 million annual green tons of softwood could produce approximately 140 tons/day of levulinic acid. The value of levulinic acid is currently over thirty times the value of black liquor.

Therefore, according to embodiments of this disclosure, suitable wood pulp products produced by an integrated method for producing wood pulp product and levulinic acid from lignocellulosic biomass include but are not limited to pulp, wood pellets, fluff pulp, dissolving pulp, other sugars such as glucose, and combustion fuel for use in producing heat.

According to another embodiment of this disclosure, the the five carbon chain sugars can be separated from the six carbon chain sugars by liquid-liquid extraction of other suitable methods known to those in the art, and instead of converting the five carbon chain sugars to furfural or other compounds, the five carbon chain sugars can be combined with the wood pulp product. In such a process, the five carbon chain sugars can function as a bonding agent for the wood pulp product. This can be particularly useful when the wood pulp product is dissolving pulp or fluff pulp.

It should be apparent that the foregoing relates only to embodiments of the present invention and that numerous changes and modifications can be made herein without departing from the scope of the invention as defined by the following claims and equivalents thereof.

We claim:

1. A method for producing levulinic acid from lignocellulosic biomass comprising hemicellulose including one or more six carbon chain compound precursors, the method comprising the steps of:
    hydrolyzing the lignocellulosic biomass in a reactor at a temperature of about 170° C. to about 185° C. for about 35 minutes to about 60 minutes to form a first phase comprising partially hydrolyzed lignocellulosic biomass including cellulose and lignin and a second phase comprising one or more five carbon chain sugars and one or more six carbon chain sugars from degradation of the hemicellulose, wherein the hydrolyzing comprises contacting the lignocellulosic biomass with at least one acid, wherein the acid is present in an amount of up to 10 percent, by weight, of the lignocellulosic biomass;
    separating the first phase from the second phase; and
    converting at least a portion of the one or more five carbon chain sugars to furfural, a furfural reaction intermediate, tar, or a combination thereof in the presence of the one or more six carbon chain sugars, by contacting the one or more five carbon chain sugars with at least one acid, wherein the acid is present in an amount of up to 10 percent, by weight, of the reactor contents; and
    separating at least a portion of the furfural, the furfural reaction intermediate, the tar, or the combination thereof from the one or more six carbon chain sugars, and thereafter
    converting at least a portion of the one or more six carbon chain sugars to levulinic acid in a reactor at a temperature of about 190° C. to about 220° C. for a period of 20 minutes to 60 minutes.

2. The method of claim 1 wherein the step of hydrolyzing the lignocellulosic biomass further comprises contacting the lignocellulosic biomass with steam, alcohol, or both.

3. The method of claim 1 wherein the first phase further comprises one or more six carbon chain sugars or one or more six carbon chain sugar precursors and the method further comprises converting the at least a portion of the one or more six carbon chain sugars or one or more six carbon chain sugar precursors from the first phase to levulinic acid.

4. The method of claim 1 wherein the second phase is liquid.

5. The method of claim 1 wherein the second phase further comprises a solvent and the method further comprises the steps of separating at least a portion of the solvent from the second phase before the step of converting at least a portion of the one or more five carbon chain sugars to furfural, a furfural reaction intermediate, tar, or a combination thereof, and recycling the at least a portion of the solvent from the second phase for use in the step of hydrolyzing the lignocellulosic biomass.

6. The method of claim 1 wherein the step of converting at least a portion of the one or more five carbon chain sugars to furfural, a furfural reaction intermediate, tar, or a combination thereof is carried out in a reactor at a temperature of about 130° C. to about 300° C. for about 35 minutes to about 60 minutes.

7. The method of claim 1 wherein separating at least a portion of the furfural from the one or more six carbon chain sugars comprises introducing the mixture of furfural and the one or more six carbon chain sugars into a flash evaporator.

8. The method of claim 1 wherein the step of converting at least a portion of the one or more six carbon chain sugars to levulinic acid comprises contacting the one or more six carbon chain sugars with at least one acid.

9. The method of claim 1 wherein the step of converting at least a portion of the one or more six carbon chain sugars to levulinic acid also converts at least another portion of the one or more six carbon chain sugars to formic acid and char.

10. The method of claim 1 further comprising converting at least a portion of the first phase to a wood pulp product.

11. The method of claim 10 wherein the wood pulp product is pulp.

12. The method of claim 11 wherein the step of converting at least a portion of the first phase to the pulp comprises converting the at least a portion of the first phase to pulp in a Kraft pulp making process.

13. The method of claim 10 wherein the wood pulp product is fuel and the step of converting at least a portion of the first phase to the wood pulp product comprises drying the at least a portion of the first phase.

14. The method of claim 10 wherein the wood pulp product is fuel and the step of converting at least a portion of the first phase to the wood pulp product comprises combusting the at least a portion of the first phase.

15. The method of claim 10 wherein the wood pulp product is wood pellets or dissolving pulp.

16. The method of claim 10 further comprising the steps of separating the five carbon chain sugars from the six carbon chain sugars and combining the five carbon chain sugars with the wood pulp product.

* * * * *